(12) United States Patent
Morishita et al.

(10) Patent No.: US 10,761,606 B1
(45) Date of Patent: Sep. 1, 2020

(54) TERMINAL DEVICE, PROGRAM, METHOD, AND SYSTEM

(71) Applicant: GungHo Online Entertainment, Inc., Tokyo (JP)

(72) Inventors: Kazuki Morishita, Tokyo (JP); Ken Narita, Tokyo (JP)

(73) Assignee: GungHo Online Entertainment, Inc. (JP)

( * ) Notice: Subject to any disclaimer, the term of this patent is extended or adjusted under 35 U.S.C. 154(b) by 0 days.

(21) Appl. No.: 16/568,925

(22) Filed: Sep. 12, 2019

Related U.S. Application Data

(63) Continuation of application No. PCT/JP2019/014734, filed on Apr. 3, 2019.

(51) Int. Cl.
*G06F 3/01* (2006.01)
*H04M 1/725* (2006.01)
*G06F 3/0481* (2013.01)
*G06F 3/02* (2006.01)
(Continued)

(52) U.S. Cl.
CPC ............... *G06F 3/015* (2013.01); *G06F 3/02* (2013.01); *G06F 3/04817* (2013.01); *H04M 1/72522* (2013.01)

(58) Field of Classification Search
CPC .... G06F 3/015; G06F 3/04842; G06F 3/0482; G06F 3/011; G06F 3/017; G06F 3/013;
(Continued)

(56) References Cited

U.S. PATENT DOCUMENTS

2009/0247895 A1\* 10/2009 Morikawa .......... A61B 5/04842
600/544
2009/0270753 A1\* 10/2009 Adachi .................. G06F 3/015
600/544
(Continued)

FOREIGN PATENT DOCUMENTS

JP 2005-085174 A 3/2005
JP 2007-202882 A 8/2007
(Continued)

OTHER PUBLICATIONS

H. Kawamura et al., "A Research Electromyographic of Reaction Time (No. 1)", Bulletin of Aichi Institute of Technology, No. 7, pp. 33-43, Mar. 30, 1972.
(Continued)

*Primary Examiner* — Dong Hui Liang
(74) *Attorney, Agent, or Firm* — Harness, Dickey & Pierce, P.L.C.

(57) ABSTRACT

A terminal device includes a pseudo input interface configured to make a user to perceive a pseudo operation, an external communication interface configured to receive intention information indicating an intention of the user from a sensor device, the sensor device being wiredly or wirelessly connected to the external communication interface, the sensor device detecting the intention of the user who intends to perform an intended operation with respect to the pseudo input interface, a memory configured to store computer readable instructions, and a processor configured to execute the computer readable instructions so as to
(Continued)

identify the intended operation by the user based on the intention information received by the external communication interface, regardless of an actual operation perceived by the user with respect to the pseudo input interface, and perform a processing corresponding to the identified intended operation.

12 Claims, 9 Drawing Sheets

(58) Field of Classification Search
CPC .............. G06F 3/04883; G06F 3/0488; G06F 3/04886; G06F 3/04817; G06F 3/04847; G06F 3/012; G06F 1/163; G06F 1/2131; G06F 21/32; G06F 2203/0381; G06F 2203/04808; A61B 5/0476; A61B 5/7475; A61B 5/048; A61B 5/04001; A61B 5/0488; A61B 5/04012; A61B 5/11

See application file for complete search history.

(56) References Cited

U.S. PATENT DOCUMENTS

| | | | |
|---|---|---|---|
| 2011/0224572 A1* | 9/2011 | Gilja | ................ A61F 4/00 600/545 |
| 2013/0158883 A1* | 6/2013 | Hasegawa | ................ A61B 5/16 702/19 |
| 2014/0078318 A1* | 3/2014 | Alameh | ................ G06F 3/017 348/207.99 |
| 2014/0210745 A1* | 7/2014 | Chizeck | ................ G06F 3/048 345/173 |
| 2016/0282940 A1 | 9/2016 | Hong et al. | |
| 2017/0123492 A1* | 5/2017 | Marggraff | ............. H04N 5/247 |

FOREIGN PATENT DOCUMENTS

| | | |
|---|---|---|
| JP | 2010-051356 A | 3/2010 |
| JP | 2013-128642 A | 7/2013 |
| JP | 2014-174880 A | 9/2014 |
| JP | 2015-156912 A | 9/2015 |
| JP | 2016-179164 A | 10/2016 |
| JP | 2017-202183 A | 11/2017 |
| JP | 2018-025888 A | 2/2018 |
| JP | 2018-190258 A | 11/2018 |

OTHER PUBLICATIONS

M. Komazaki, "A Study of Human Pointing Features on Touch-Screens", doctoral thesis at the University of Electro-Communications, 10 pages, Sep. 2008.

* cited by examiner

| OPERATION INPUT ID | FEATURE POINT | OPERATION CONTENT |
|---|---|---|
| O1 | T1 | TOUCH |
| O2 | T2 | LONG PRESS |
| O3 | T3 | SWIPE |
| O4 | T4 | DOUBLE TOUCH |
| O5 | T5 | PRESS HARDWARE KEY |
| ... | ... | ... |

FIG. 4B

| PROCESSING ID | OPERATION INPUT ID | CONTENT OF PROCESSING |
|---|---|---|
| P1 | O1 | TRANSITION TO NEXT SCREEN |
| P2 | O2 | DISPLAY TITLE SCREEN |
| P3 | O3 | DISPLAY SETTING SCREEN |
| P4 | O4 | RESET |
| P5 | O5 | FINISH APPLICATION |
| ... | ... | ... |

| OPERATION INPUT ID | FEATURE POINT | OPERATION CONTENT |
|---|---|---|
| Q1 | S1 | TOUCH ICON 21 |
| Q2 | S2 | LONG-PRESS ICON 21 |
| Q3 | S3 | TOUCH ICON 22 |
| Q4 | S4 | LONG-PRESS ICON 22 |
| Q5 | S5 | SWIPE ICON 22 |
| ... | ... | ... |

| OPERATION INPUT ID | FEATURE POINT | OPERATION CONTENT |
|---|---|---|
| I1 | Q1 | DISPLAY START SCREEN |
| I2 | Q2 | USER CHANGE |
| I3 | Q3 | DISPLAY SETTING SCREEN |
| I4 | Q4 | RESET SETTING |
| I5 | Q5 | FINISH APPLICATION |
| ... | ... | ... |

FIG. 10A

| OPERATION INPUT ID | FEATURE POINT | OPERATION CONTENT |
|---|---|---|
| R1 | U1 | OPERATION OF UP ARROW KEY |
| R2 | U2 | OPERATION OF DOWN ARROW KEY |
| R3 | U3 | OPERATION OF LEFT ARROW KEY |
| R4 | U4 | OPERATION OF RIGHT ARROW KEY |
| R5 | U5 | INPUT OF KEY 1 |
| ... | ... | ... |
| R14 | U14 | INPUT OF KEY 0 |

FIG. 10B

| OPERATION INPUT ID | FEATURE POINT | OPERATION CONTENT |
|---|---|---|
| V1 | R1 | UPWARD MOVEMENT OF CURSOR |
| V2 | R2 | DOWNWARD MOVEMENT OF CURSOR |
| V3 | R3 | LEFT MOVEMENT OF CURSOR |
| V4 | R4 | RIGHT MOVEMENT OF CURSOR |
| V5 | R5 | INPUT OF NUMBER 1 |
| ... | ... | ... |
| V14 | R14 | INPUT OF NUMBER 0 |

TERMINAL DEVICE, PROGRAM, METHOD, AND SYSTEM

CROSS-REFERENCE TO RELATED APPLICATIONS

The present application is a continuation application of International Application No. PCT/JP2019/014734, filed on Apr. 3, 2019, which is expressly incorporated herein by reference in its entirety.

BACKGROUND

1. Technical Field

The present disclosure relates to a terminal device, a program, a method, and a system which use a detected intention of the user.

2. Related Art

When a human receives external stimulus, the human perceives the stimulus with a sensory receptor, judges the stimulus, designs what to do, and finally contracts peripheral muscles to take action. Generally, it is known that it takes 200 milliseconds to take the action after reception of the stimulus even in a case where there is no load (Hitoshi Kawamura et al. "A Research Electromyographic of Reaction Time (No. 1)", Bulletin of Aichi Institute of Technology No. 7, Mar. 30, 1972, p 33-43).

A terminal device, such as a smartphone, is operated under the condition that judgement is required for various stimuli received from various factors other than the terminal device. Therefore, it is readily conceivable that it takes 200 milliseconds or more to input an instruction after receiving a stimulus from a display.

Furthermore, in an input interface, it is necessary to perform tasks, such as moving, positioning, and touching (click) of fingers or a mouse, even after contracting the muscles to start the action. Therefore, it is known that it takes 200 milliseconds to 1,200 milliseconds to complete all the tasks (Masanobu Komazaki, "A Study of Human Pointing Features on Touch-Screens", Doctor Thesis, The University of Electro-Communications, September 2008).

Meanwhile, it has been known that detection and measurement of a brain wave of a user enable to measure an intention of the user on the basis of the measured brain wave to operate various devices. For example, in JP 2007-202882 A, it is stated that a user's attention area and attention degree are measured on the basis of a brain wave of the user to control a movement direction and speed of an electric wheelchair.

SUMMARY

On the basis of the technology as described above, the present disclosure provides a terminal device, a program, a method, and a system according to various embodiments which perform an operation input more readily than a user actually operates an input interface by using information on an intention of the user.

According to an aspect of the present disclosure, provided is "a terminal device comprising: a pseudo input interface configured to receive a pseudo operation by a user; an external communication interface configured to receive, from a sensor device wiredly or wirelessly connected to detect an intention of the user who intends to perform an operation on the pseudo input interface, intention information indicating the intention of the user detected by the sensor device; a memory configured to store a computer readable instructions; and a processor configured to execute the computer readable instructions so as to: identify an operation by the user based on the intention information received by the external communication interface, regardless of an actual operation performed on the pseudo input interface by the user; and perform processing corresponding to the identified operation".

According to an aspect of the present disclosure, provided is "a computer program product embodying computer readable instructions stored on a non-transitory computer-readable storage medium for causing a computer including: a pseudo input interface configured to receive a pseudo operation by a user; an external communication interface configured to receive, from a sensor device wiredly or wirelessly connected to detect an intention of the user who intends to perform an operation on the pseudo input interface, intention information indicating the intention of the user detected by the sensor device; and a memory, the computer configured to perform the steps of: identifying an operation by the user based on the intention information received by the external communication interface, regardless of an actual operation performed on the pseudo input interface by the user; and performing processing corresponding to the identified operation".

According to an aspect of the present disclosure, provided is "a method for causing a processor in a computer to execute a process, the computer including: a pseudo input interface configured to receive a pseudo operation by a user; an external communication interface configured to receive, from a sensor device wiredly or wirelessly connected to detect an intention of the user who intends to perform an operation on the pseudo input interface, intention information indicating the intention of the user detected by the sensor device; and a memory configured to store the computer readable instructions, the method comprising executing the computer readable instructions on the processor the steps of: identifying an operation by the user based on the intention information received by the external communication interface, regardless of an actual operation performed on the pseudo input interface by the user; and performing processing corresponding to the identified operation.

According to an aspect of the present disclosure, provided is "a system including the above terminal device; and a sensor device wiredly or wirelessly connected to the terminal device to detect an intention of a user performing one or a plurality of operation inputs to an input interface of the terminal device".

According to an aspect of the present disclosure, provided is "a system including the terminal device described above, and a sensor device wiredly or wirelessly connected to the terminal device to detect an intention of the user performing one or a plurality of operation inputs to an input interface of the terminal device".

According to an aspect of the present disclosure, provided is "a terminal device comprising: a pseudo input interface configured to receive a pseudo operation by a user; an external communication interface wiredly or wirelessly connected to receive a signal indicating an intention of the user performing an operation on the pseudo input interface; a memory configured to store computer readable instructions and a correspondence relationship between the signal and the intention of the user; and a processor configured to execute the computer readable instructions so as to: generate intention information on the intention of the user based on the received signal and the correspondence relationship stored in the memory, regardless of an actual operation performed on the pseudo input interface by the user, identify an operation by the user from the generated intention information, and execute processing corresponding to the identified operation".

According to various embodiments of the present disclosure, a terminal device, a program, a method, and a system are provided to perform an operation input more readily than a user actually operates an input interface by using information on an intention of the user.

It should be noted that the above effects are by way of example only for ease of description and the present disclosure is not limited to the description. In addition to or in place of the above effects, any effect described in the present disclosure or apparent for those skilled in the art can be also provided.

BRIEF DESCRIPTION OF DRAWINGS

FIG. 4B is a table conceptually illustrating a processing identification table stored in a memory 113 of a terminal device 100 according to the first embodiment of the present disclosure.

FIG. 10A is a table conceptually illustrating an operation identification table stored in a memory 212 of a brain wave sensor device 200 according to the third embodiment of the present disclosure. FIG. 10B is a table conceptually illustrating a processing identification table stored in a memory 113 of a terminal device 100 according to the third embodiment of the present disclosure.

DESCRIPTION OF EXEMPLARY EMBODIMENTS

Figure 1:
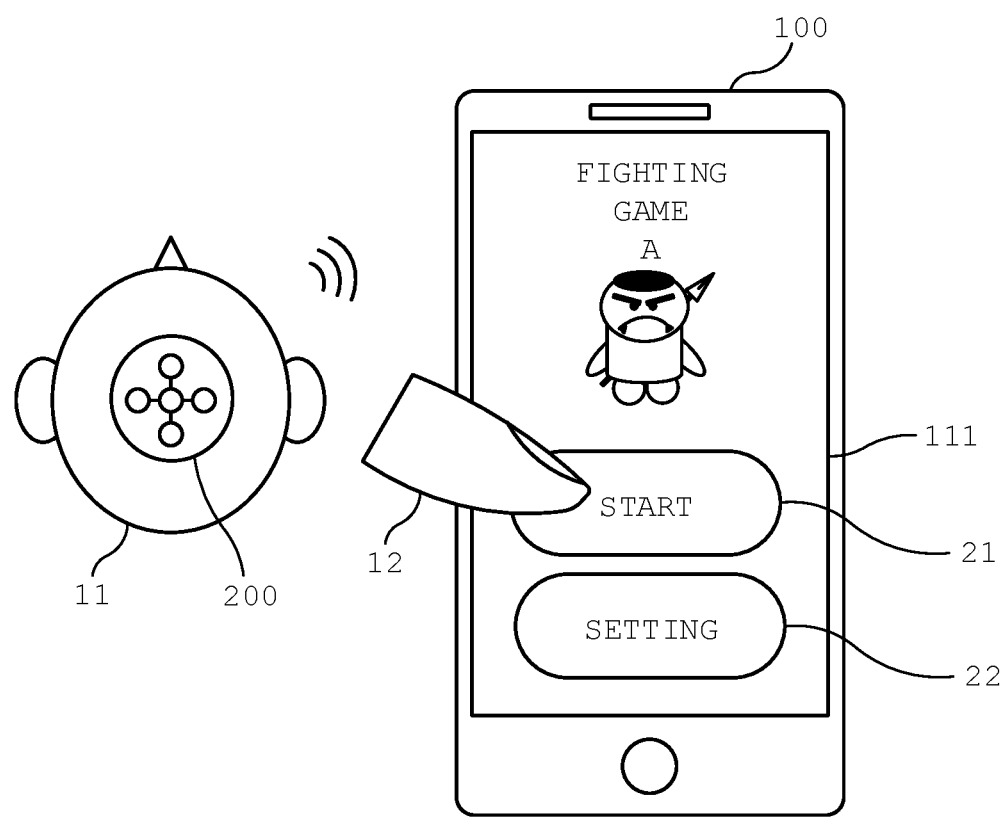
FIG. 1 is a diagram conceptually illustrating processing in a system according to various embodiments of the present disclosure.

Various embodiments of the present disclosure will be described with reference to the accompanying drawings. In addition, the same referential marks are given to common components in the drawings.

Overview of System Relating to Present Disclosure

FIG. 1 is a diagram conceptually illustrating processing in a system according to various embodiments of the present disclosure. According to FIG. 1, the system is configured to detect an intention of a user 11 to perform an operation input on the basis of a brain wave detected by a brain wave sensor device 200 mounted to the user 11 and perform processing corresponding to the operation which the user 11 intends to input, according to a result of the detection.

Here, in general, in a terminal device, such as a smartphone, an input interface with which a user operates the terminal device is a very important component. For example, only detection of an intention of the user on the basis of his/her brain wave and operation of the terminal device according to the detected intention are required to obtain a user's desired result, such as transition to a screen which the user desires to view. However, in that case, since the user performs no operation on the terminal device, it is difficult for the user to obtain the feeling of operating the terminal device, and a poor operational feeling is provided. In order to obtain a satisfactory operational feeling, it is important for the user to perceive that the user him/herself operates, for example, "pushes" or "touches", the input interface of the terminal device.

Therefore, in a terminal device of the present disclosure, an intention of a user is detected on the basis of his/her brain wave, and processing is performed according to the detected intention. Meanwhile, the terminal device includes a pseudo input interface to cause the user operating the terminal device to perceive operation, such as "pressing" or "touching", on the terminal device.

In the system illustrated as an example in FIG. 1, a display 111 of a terminal device 100 is caused to display icons 21 and 22 thereon. The icons 21 and 22 are displayed to cause the user to perceive in a pseudo manner that processing assigned to each of the icons will be performed when the user touches the icons 21 and 22 with a pointer 12. Therefore, even if the user actually touches the icons 21 and 22, processing is not always performed with the touching as a trigger.

On the other hand, when the brain wave sensor device 200 mounted to the user 11 detects an intention of the user 11 to operate any of the icons 21 and 22 displayed on the display 111, information on the intention is transmitted to the terminal device 100. When the terminal device 100 receives the information, the terminal device 100 performs processing associated with any of the icons 21 and 22. In other words, the processing associated with the icon 21 or 22 is performed on the basis of the information on the detected intention, even though it is not detected that the user 11 actually touches the icon with the pointer 12.

In the present disclosure, the "pseudo input interface" represents an input interface which is not treated as a trigger for performance of processing, even though an operation, such as touching or pressing, is performed. Thus, in FIG. 1, the icons displayed on the display 111 are given as an example of the "pseudo input interface". However, the "pseudo input interface" is not limited to the icons and may be another displayed object displayed on the display 111, the display 111 itself, or a hardware key fixedly provided on a housing of the terminal device 100.

Moreover, it is not necessary to always treat the "pseudo input interface" as the trigger even when an operation, such as touching or pressing, is performed. In other words, the pseudo input interface is desirably configured not to be treated as a trigger only when a user intention detection function is on, according to a mode of the terminal device 100, an activated function/application, a selection by the user, or the like. Therefore, in the other case, the pseudo input interface may function as the input interface serving as the trigger to perform predetermined processing when an operation is received.

FIRST EMBODIMENT

Figure 2:
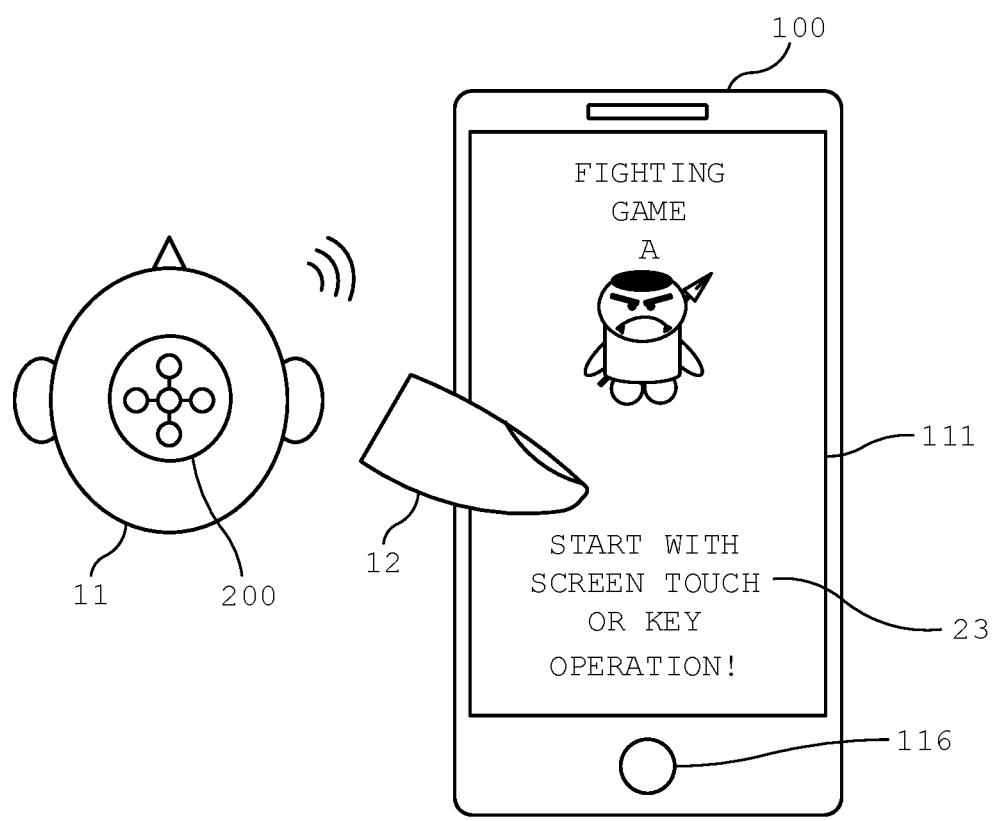
FIG. 2 is a diagram conceptually illustrating processing in a system according to a first embodiment of the present disclosure.

1. Configuration of System 1 According to First Embodiment of Present Disclosure FIG. 2 is a diagram conceptually illustrating processing in a system according to a first embodiment of the present disclosure. According to FIG. 2, when an intention of a user 11 to touch a display 111 functioning as a pseudo input interface or press a hardware key 116 is detected from a brain wave by using a brain wave sensor device 200 mounted to the user 11, communication with a server device 300 is started, and necessary information is transmitted and received. At this time, communication with the server device 300 is performed on the basis of the detected intention of the user 11, requiring no actual detection of touching the display 111 or pressing a hardware key 116 with a pointer 12 of the user 11. In other words, regardless of whether the user touches the display 111 or presses the hardware key 116, processing corresponding to the detected intention is performed.

Figures 3, 4A:
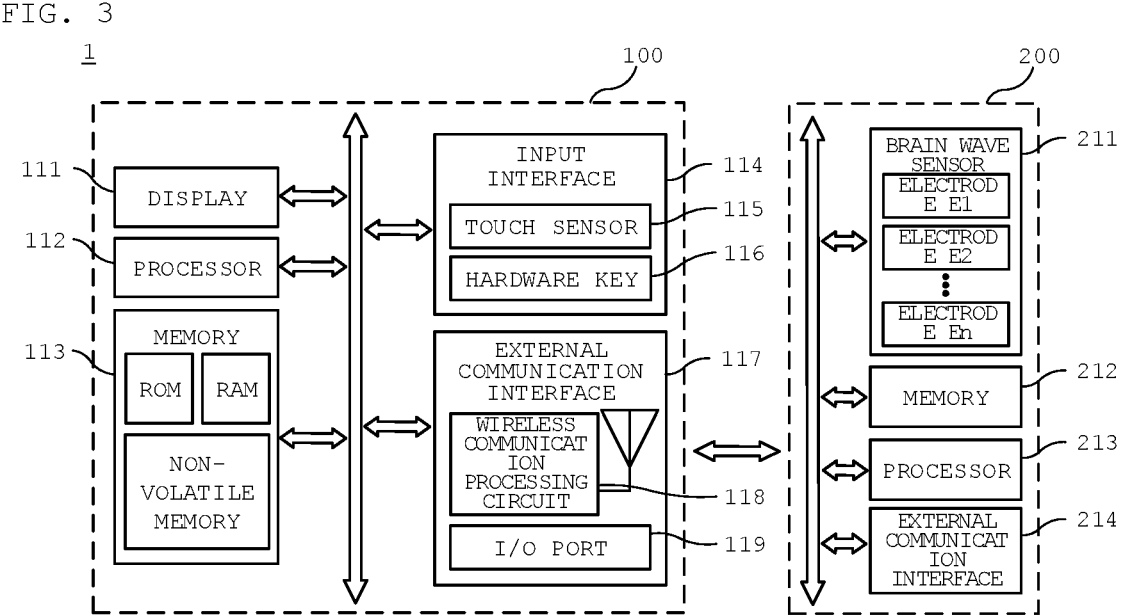
FIG. 3 is a block diagram illustrating an example of a configuration of a system 1 according to the first embodiment of the present disclosure.
FIG. 4A is a table conceptually illustrating an operation identification table stored in a memory 212 of a brain wave sensor device 200 according to the first embodiment of the present disclosure.

FIG. 3 is a block diagram illustrating an example of a configuration of the system 1 according to the first embodiment of the present disclosure. Referring to FIG. 3, the system 1 includes a terminal device 100 and the brain wave sensor device 200 communicably connected to the terminal device 100 wiredly or wirelessly. The terminal device 100 and the brain wave sensor device 200 do not need to have all of the components illustrated in FIG. 3, some of the components may be omitted, or another component may be added.

An example of the terminal device 100 includes a portable terminal device, such as a smartphone, capable of wireless communication. However, in addition, the system 1 according to the present embodiment can be preferably applied to a device, such as a handheld game console, feature phone, personal digital assistant, PDA, laptop personal computer, desktop personal computer, stationary game console, music player, printer such as multifunctional peripherals or laser printer, controller for a machine tool or manufacturing machine, car navigation system or vehicle equipment, as long as the device is configured to input and output information to and from another device or module and receive an operation input from the user.

According to FIG. 3, the terminal device 100 includes the display 111, a processor 112, a memory 113, an input interface 114 including a touch sensor 115 and the hardware key 116, and an external communication interface 117 including a wireless communication processing circuit 118 connected to an antenna and an I/O port 119. Then, these components are electrically connected to each other via a control line and a data line.

The display 111 functions as a display unit to read image information stored in the memory 113 for various display, in response to an instruction from the processor 112. Specifically, for example, in the example of FIG. 2, immediately after a game application is started, the display 111 displays a title screen for receiving a start operation from the user on a screen. Furthermore, although not particularly illustrated, when an operation input to the touch sensor 115 or the hardware key 116 is received on the title screen, a start screen of the game application is displayed. Moreover, these displays cause the user 11 to perceive the possibility of operation on the display 111, and the display 111 itself functions as the pseudo input interface. For example, the display 111 is constituted by a liquid crystal display.

The processor 112 includes a CPU (microcomputer) and functions as a control unit to control other components connected, on the basis of various programs stored in the memory 113. The processor 112 executes an instruction, that is, a program for a game application according to the present embodiment or a program for executing an OS, stored in the memory 113. Specifically, the processor 112 identifies an operation by the user from intention information indicating an intention of the user to "perform an operation input" received from the brain wave sensor device 200 and executes processing corresponding to the identified operation. Furthermore, in some cases, when an operation input performed by the user is received by the input interface 114, the processor 112 may perform processing corresponding to operation information identified on the basis of the operation input. The processor 112 may be constituted by a single CPU but may be constituted by a plurality of CPUs. Furthermore, another type of processor, such as a GPU, may be combined as appropriate.

The memory 113 includes a RAM, a ROM, and a non-volatile memory (in some cases, an HDD) and functions as a storage unit. The ROM stores, as a program, an instruction for executing the application or the OS according to the present embodiment. The RAM is a memory used to write and read data while a program stored in the ROM is being executed by the processor 112. The non-volatile memory is a memory to/from which data is written/read upon execution of the program, and the data written to the non-volatile memory is stored even after the execution of the program is completed. Furthermore, the memory 113 stores a processing identification table (FIG. 4B) in which information about an operation detected by the brain wave sensor device 200 is associated with the content of processing performed on the basis of the operation.

The input interface 114 includes the touch sensor 115 and the hardware key 116 and functions as an input unit to receive various operation inputs from the user. The touch sensor 115 is used to receive various operation inputs from the user, such as an operation of an icon displayed on the display 111 and an input of a character string by the user. The touch sensor 115 is disposed so as to cover the display 111 and outputs information about proximity coordinates or contact coordinates of the pointer 12 (user's finger, a stylus, or the like), corresponding to image data displayed on the display 111. The touch sensor of known type, such as a resistive type, a capacitive type, or a surface acoustic wave type, may be employed. In the present embodiment, the touch sensor 115 of capacitive type is preferably used to detect the proximity of the pointer 12 of the user. The hardware key 116 uses a well-known hardware key.

In the present embodiment, the pseudo input interface is provided to perform processing on the basis of a brain wave detected by the brain wave sensor device 200. Therefore, the input interface 114 is not necessarily provided. The input interface 114 may be provided to be used along with processing based on the brain wave sensor device 200, or processing based on the input interface 114 may be performed only when no processing based on the brain wave sensor device 200 is to be performed.

Furthermore, in the present embodiment, the display 111 is caused to function as the pseudo input interface. However, the input interface 114 may also be caused to function as the pseudo input interface without using the received operation as the trigger for processing.

The external communication interface 117 includes the wireless communication processing circuit 118, the antenna connected to the wireless communication processing circuit, and the I/O port 119 and functions as a communication unit. The external communication interface 117 transmits and receives programs necessary for execution of various applications, user information, drawing information, and the like to and from the server device 300 installed remotely and connected via a network. In particular, in the present embodiment, the information on the intention of the user who performs an operation input is received from the brain wave sensor device 200.

The wireless communication processing circuit 118 and the antenna are operated on the basis of a wide band wireless communication system, such as wideband-code division multiple access (W-CDMA) system or a long term evolution (LTE) system but may be operated on the basis of a wireless LAN, such as IEEE 802.11, or a narrow band wireless communication system, such as Bluetooth (registered trademark).

The I/O port 119 is connected to an I/O port of an external device wiredly connected. The I/O port 119 can adopt a desired connection, such as a serial port, parallel port, or USB.

In the present embodiment, various information including the intention information are transmitted and received to and from the brain wave sensor device 200, but this transmission and reception may be performed by any of wireless communication via the wireless communication processing circuit 118 and wired communication via the I/O port 119. When the terminal device 100 according to the present embodiment is used, it takes 200 milliseconds or more to perceive a stimulus by a sensory receptor (perceive information displayed on the display 111), make a decision, determine an operation input, and finally contract peripheral muscles to take action (operation input to the touch sensor 115). Therefore, in consideration of the time, a communication system having a higher communication rate is preferably employed for communication with the brain wave sensor device 200, but the communication rate above a certain level is preferably required, and the communication system is selected appropriately from the viewpoint of communication stability and communication rate.

Furthermore, according to FIG. 3, the brain wave sensor device 200 includes a brain wave sensor 211 including one or a plurality of electrodes El to En, a memory 212, a processor 213, and an external communication interface 214. Then, these components are electrically connected to each other via a control line and a data line.

The brain wave sensor 211 includes one or a plurality of electrodes El to En. It is known that, in the brain, cerebral cortex generally controls the functions of perception, voluntary movement, thinking, guessing, and the like, and areas of the cerebral cortex play different roles depending on the areas. For example, in order to perform an operation input to the terminal device 100 with a finger, the functions of the orbital frontal cortex, motor association cortex, and primary motor cortex are required. Thus, the electrodes El to En are arranged at positions on the scalp corresponding to these active areas. The arrangement and the number of the electrodes El to En may be determined in advance by sampling the brain waves of the user by using the brain wave sensor device 200 and appropriately selecting an electrode from which the strongest peak monitored upon operation to the input interface 114 is detected. An analog signal output from each of the electrodes El to En is appropriately converted into a digital signal and used for subsequent processing.

The memory 212 includes a RAM, a ROM, a non-volatile memory, and the like and functions as a storage unit. The ROM stores, as a program, an instruction for controlling the brain wave sensor 211 according to the present embodiment or transmitting or receiving information to or from the terminal device 100. The RAM is a memory used to write and read data while a program stored in the ROM is being executed by the processor 213. The non-volatile memory is a memory to/from which data is written/read upon execution of the program, and the data written to the non-volatile memory is stored even after the execution of the program is completed. In the present embodiment, the memory 212 stores an operation identification table (FIG. 4A) in which a feature point of a brain wave detected when the user intends to operate the pseudo input interface is associated with the content of processing performed when the feature point is detected.

The processor 213 includes a CPU (microcomputer) and functions as a control unit to control another component connected, on the basis of various programs stored in the memory 212. The processor 213 executes a program for carrying out an instruction stored in the memory 212. Specifically, the processor 213 refers to a brain wave signal output from the brain wave sensor 211 and the operation identification table, determines a matching point with a feature point of a brain wave signal sampled in advance, and determines a content of operation which the user intends to input.

The external communication interface 214 functions as a communication unit configured to be used to transmit and receive information to and from the terminal device 100. Accordingly, the external communication interface 214 appropriately includes a wireless communication processing circuit 118, an antenna connected to the wireless communication processing circuit, and an I/O port 119, corresponding to the external communication interface 117 of the terminal device 100.

2. Information Stored in Memory 212

FIG. 4A is a table conceptually illustrating the operation identification table stored in the memory 212 of the brain wave sensor device 200 according to the first embodiment of the present disclosure. Specifically, the table stores feature points of brain wave signals of the user who performs operation inputs in a pseudo manner, sampled in advance, and the table is used to determine that the user intends to perform what kind of pseudo operation. According to FIG. 4A, an item of feature point information and an item of operation content information are stored in association with each item of operation input ID information. The brain waves of the user are sampled in advance when the user performs various operation inputs to the display 111 functioning as the pseudo input interface. The feature point information is information on a characteristic peak of a pseudo operation identified on the basis of a waveform obtained from each of the sampled brain waves. The operation content information is information indicating the content of a pseudo operation performed by the user when each item of the feature point information is obtained. In the present embodiment, for example, a feature point of a brain waveform detected by the brain wave sensor 211 is compared with each feature point stored in the operation identification table of FIG. 4A, and when the feature point of the detected brain waveform matches feature point information "Ti", a "touch" input is identified as pseudo operation content information. Then, from the brain wave sensor device 200, operation input ID information "O1" corresponding to the "touch" input is output as intention information to the terminal device 100.

FIG. 4B is a table conceptually illustrating the processing identification table stored in the memory 113 of the terminal device 100 according to the first embodiment of the present disclosure. Specifically, the table stores the operation input ID information received as the intention information from the brain wave sensor device 200, in association with the content of processing identified on the basis of the operation input ID information. According to FIG. 4B, an item of the operation input ID information and the content of processing are stored in association with each item of processing ID information. The operation input ID information is information in which a pseudo operation which the user intends to input is identified by the brain wave sensor device 200. The processing content information is information indicating the content of processing executed by the processor 112 on the basis of a predetermined pseudo operation having been performed on the pseudo input interface by the user. In the present embodiment, for example, when an item of the operation input ID information "O1" is received from the brain wave sensor device 200, the processor 112 refers to the processing identification table, determines processing content information ("transition to next screen") associated with an item of the operation input ID information "O1", and executes processing (communication with the server device 300, drawing processing, etc.) to transition to the next screen.

3. Processing Sequence Between Devices

Figure 5:
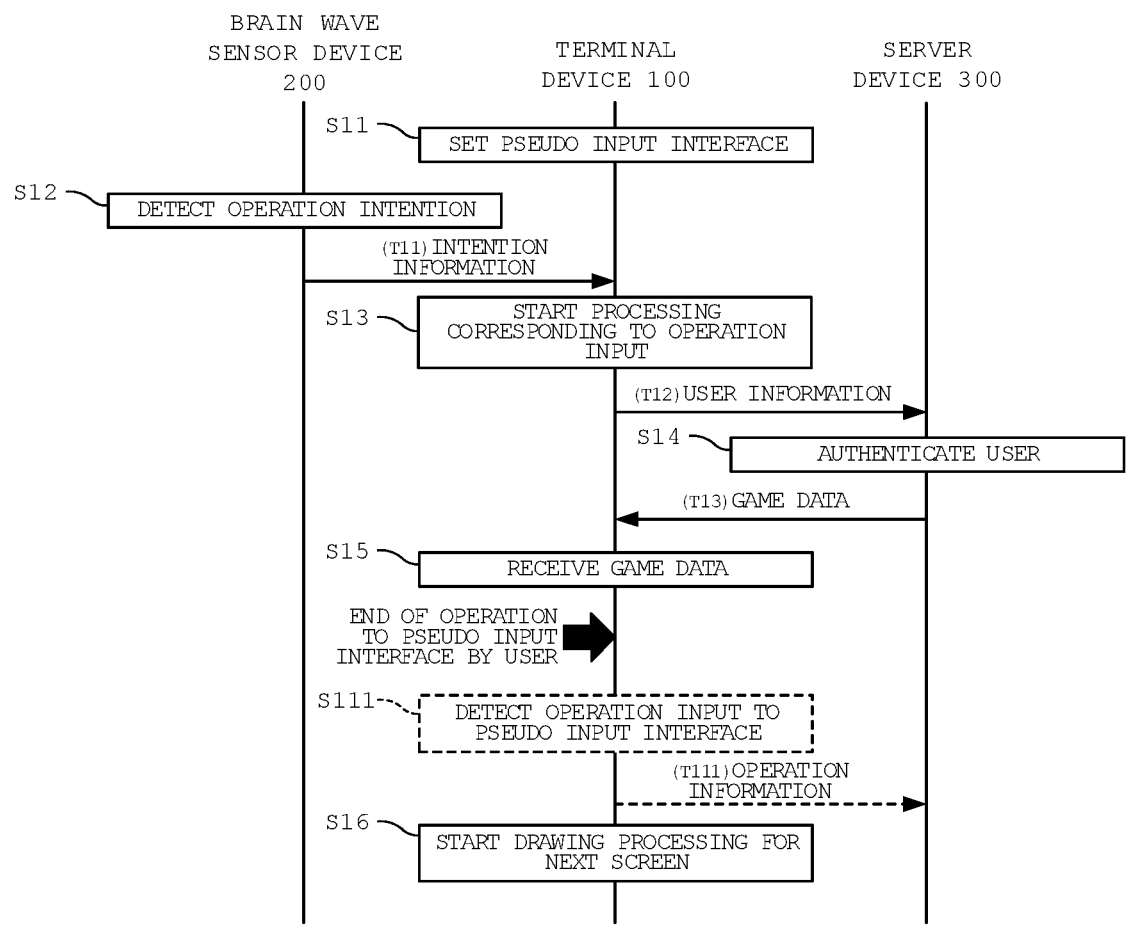
FIG. 5 is a diagram illustrating a processing sequence performed between the terminal device 100, the brain wave sensor device 200, and a server device 300 according to the first embodiment of the present disclosure.

FIG. 5 is a diagram illustrating a processing sequence performed between the terminal device 100, the brain wave sensor device 200, and a server device 300 according to the first embodiment of the present disclosure. Specifically, FIG. 5 illustrates an example of an operation input performed when a game application "fighting game A" shown in FIG. 2 is activated and a title screen is displayed, on the terminal device 100. FIG. 5 shows a sequence of interruption processing started by detecting an intention of the user to perform an operation input and transmitting intention information generated on the basis of the detection, by the brain wave sensor device 200. FIG. 5 illustrates an example of transmission and reception of information to and from the server device 300 performed by operation input on the title screen of FIG. 2. This, however, merely shows an example. In other words, the user may be caused to perceive the situation through not only the title screen but also another component. Furthermore, processing not using the server device 300 may be performed or processing by using another server device or another terminal device may be performed.

In FIG. 5, when the title screen is displayed on the display 111, the terminal device 100 sets the display 111 and the hardware key 116 as the pseudo input interface (S11). The user who perceives the pseudo input interface through the display 111 determines whether to touch the display 111 or press the hardware key 116. Then, as a result of the determination, the user makes a decision to touch (operate) the display 111 to cause a transition to a start screen. During making this decision, the processor 213 of the brain wave sensor device 200 monitors feature points of waveforms output from the brain wave sensor 211 having the electrodes El to En as needed (S12). Each time each of the feature points is obtained, the processor 213 refers to the operation identification table illustrated in FIG. 4A and determines matching of the obtained feature point with a feature point of an operation input performed by the user, sampled in advance. When the feature points do not match, the processor 213 returns to monitoring a waveform again.

On the other hand, when the feature points match, the processor 213 refers to operation content information associated with the feature point matching the obtained feature point and identifies the content of the operation input which the user intends to perform. In the present embodiment, as described above, a decision made by the user to perform an operation input to touch the touch sensor 115 matches the feature point of an item of operation input ID information "O1". Therefore, the processor 213 generates an item of the intention information including at least an item of the operation input ID information "O1" and performs control so as to transmit the intention information (T11) to the terminal device 100 via the external communication interface 214.

Next, the terminal device 100 refers to the processing identification table illustrated in FIG. 4B and starts processing associated in advance with the operation input ID information received as the intention information (S13). In the present embodiment, firstly, the terminal device 100 transmits user information (T12) stored in the memory 113 to the server device 300. Then, the server device 300 having received the user information authenticates the user (S14), and when the user is authenticated as a valid user of the game application "fighting game A", game data (T13) of the user stored in the server device 300 is transmitted to the terminal device 100.

The terminal device 100 sequentially receives the game data transmitted from the server device 300 (S15). When the reception of the game data is completed, the terminal device 100 starts drawing processing for displaying the start screen on the display 111 by using the received game data or drawing information on the start screen stored in the memory 113 (S16).

Here, in the present embodiment, detection of actual touching or pressing the display 111 or hardware key 116 functioning as the pseudo input interface is not required, in this process. That is, regardless of the presence or absence of the actual operation of the display 111 and hardware key 116, the terminal device 100 performs the processing according to S13 to S16, on the basis of the operation input ID information received as the intention information. In other words, even if the user's actual operation on the display 111 or hardware key 116 functioning as the pseudo input interface is finished after the detection of the intention to perform the operation, the terminal device 100 does not perform detection of the actual operation input (S111) or does not transmit operation information (T111) to the server device 300 triggered with the actual operation input as a trigger.

4. Process Performed in Terminal Device 100

Figure 6:
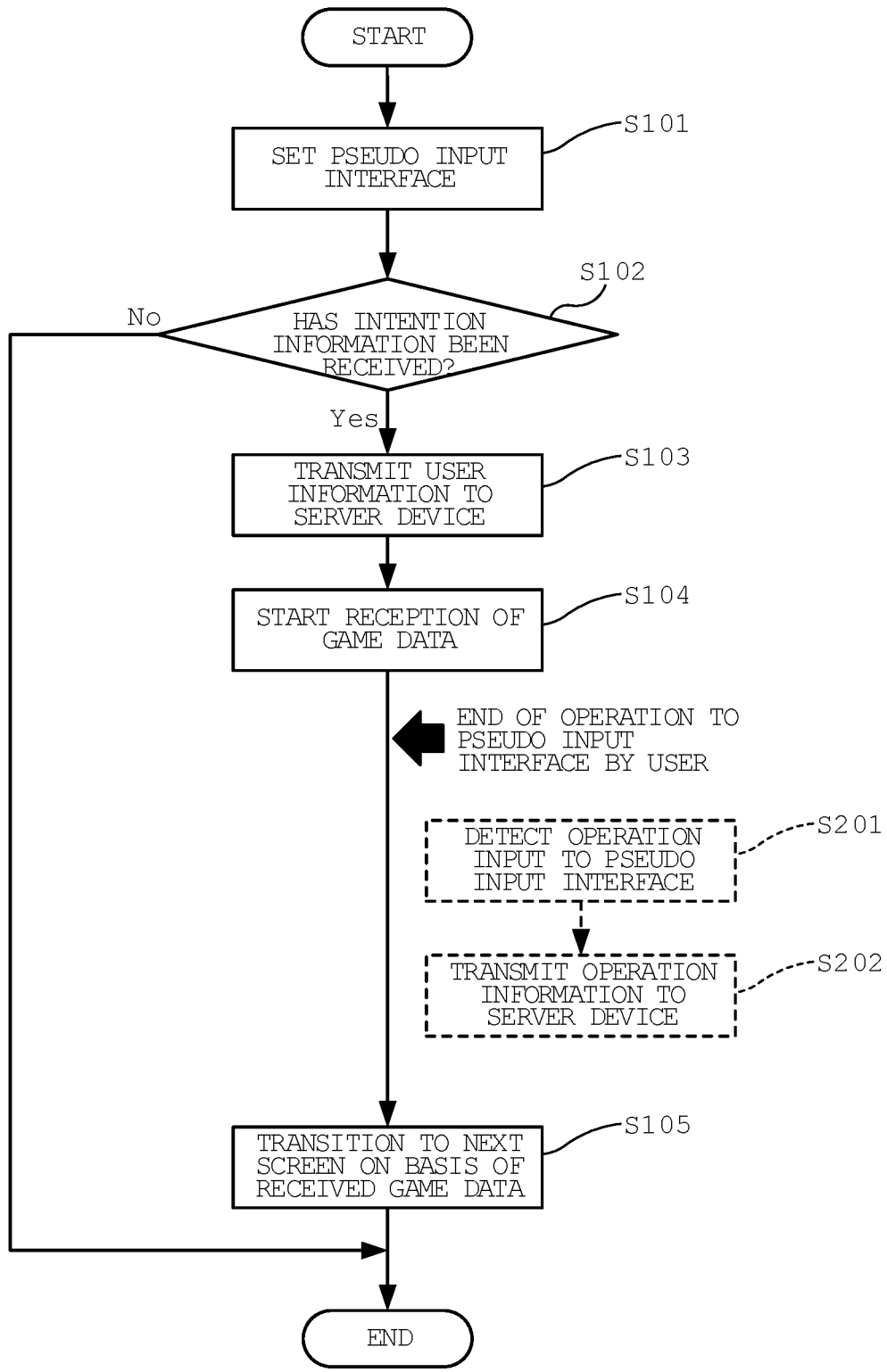
FIG. 6 is a flowchart illustrating a process performed in the terminal device 100 according to the first embodiment of the present disclosure.

FIG. 6 is a flowchart illustrating a process performed in the terminal device 100 according to the first embodiment of the present disclosure. Specifically, the process relates to interruption processing started by receiving intention information from the brain wave sensor device 200.

According to FIG. 6, the processor 112 displays the title screen illustrated in FIG. 2 on the display 111, sets the display 111 and the hardware key 116 as the pseudo input interface, and starts the process (S101). Then, the processor 112 determines whether operation input ID information is received as intention information from the brain wave sensor device 200 via the external communication interface 117 (S102). Then, when the intention information is received, on the basis of the operation input ID information, pseudo operation which the user is about to perform is identified as touching the display 111. Then, processing associated with the pseudo touch operation is performed on the title screen.

Specifically, the processor 112, firstly, controls the external communication interface 117 to transmit user information stored in the memory 113 to the server device 300 (S103). Then, the processor 112 controls the server device 300 to authenticate the user and start reception of game data necessary to execute the game application (S104). Next, the processor 112 starts drawing the next screen (start screen) sequentially on the basis of the received game data and drawing information stored in the memory 113 (S105).

Here, in the present embodiment, detection of actual touching or pressing the display 111 or hardware key 116 functioning as the pseudo input interface is not required, in this process. That is, regardless of the presence or absence of the actual operations on the display 111 and hardware key 116, the processor 112 executes the processing according to S103 to S105, on the basis of the operation input ID information received as the intention information. In other words, even if the user's actual operation on the display 111 or hardware key 116 functioning as the pseudo input interface is finished after the detection of the intention to perform the operation, the terminal device 100 does not perform detection of the actual operation input (S201) or does not perform transmission of operation information to the server device 300 (S202) with the actual operation input as a trigger.

Note that when the intention of the user to perform the pseudo operation on the pseudo input interface is detected and the operation content thereof is identified, feedback according to the identified operation may be given to the user. Specifically, the memory 113 stores a feedback table in which feedback to be given is associated with each identified operation input ID. Then, when the operation content is identified by receiving the operation input ID information, the processor 112 refers to the table and determines the feedback according to the identified operation. Examples of the feedback include vibration drive using a vibration motor, lighting of an LED, display of an indicator on a screen, and the like.

As described above, in the present embodiment, the brain wave sensor device 200 detects an intention of the user to perform an operation, and thereby it is possible to cause the terminal device 100 to perform corresponding processing. Meanwhile, the terminal device 100 includes the display 111 and the hardware key 116 which function as the pseudo input interface, and although the execution of the processing itself is performed on the basis of the intention detected by the brain wave sensor device 200, it is possible to give an operational feeling to the user as if he/she actually operates the device 100.

SECOND EMBODIMENT

In the first embodiment, the entire display 111 and the hardware key 116 which function as the pseudo input interface in the title screen have been described. That is, a description has been given of the brain wave sensor device 200 detecting the intention of the user to perform the pseudo operation on the display 111 or hardware key 116 to perform the processing on the basis of the detected intention. In a second embodiment, a description will be given of a display 111, not the whole area of which is caused to function as a pseudo input interface but a partial area of which is caused to function as the pseudo input interface. Note that the present embodiment is similar to the first embodiment in configuration, processing, and procedure, except for the points described below specifically. Therefore, detailed description thereof will be omitted.

Figures 7, 8A:
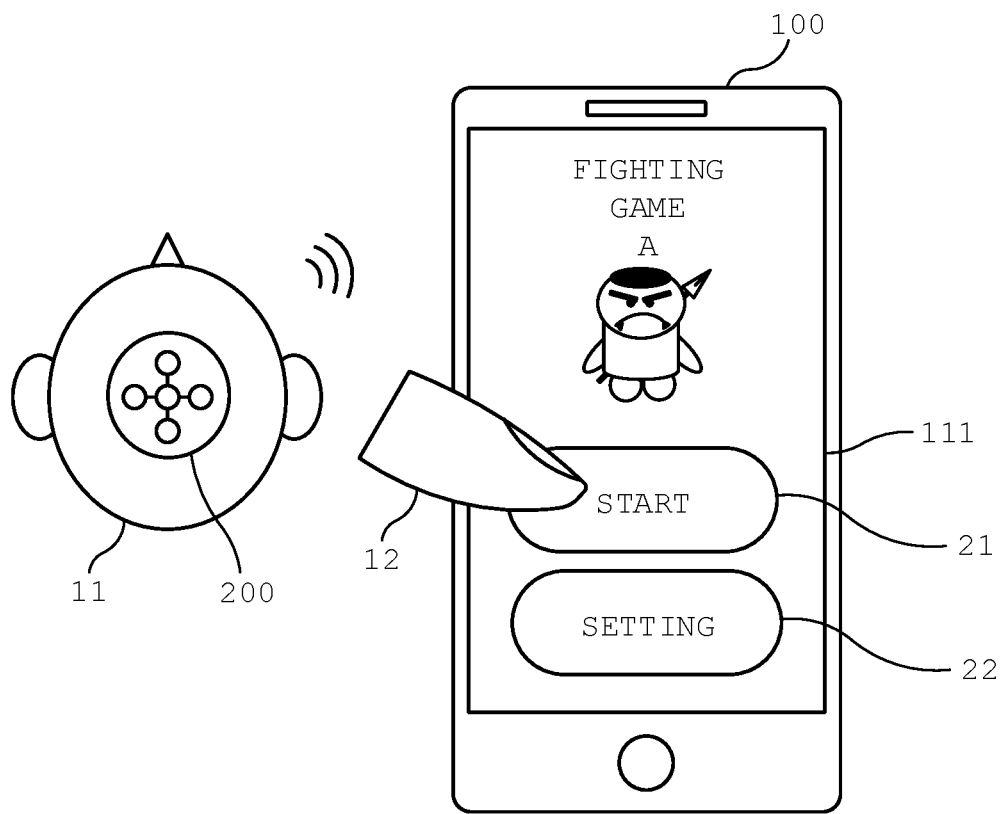
FIG. 7 is a diagram conceptually illustrating processing in a system according to a second embodiment of the present disclosure.
FIG. 8A is a table conceptually illustrating an operation identification table stored in a memory 212 of a brain wave sensor device 200 according to the second embodiment of the present disclosure.

FIG. 7 is a diagram conceptually illustrating processing in a system according to the second embodiment of the present disclosure. According to FIG. 7, one or a plurality of icons (icons 21 and 22) are displayed in at least partial areas of the display 111. In the present embodiment, the areas in which the icons 21 and 22 are displayed are caused to function as the pseudo input interface, and the other area in which, for example, "fighting game A" is displayed is not caused to function as the pseudo input interface but to merely function as a display area.

Firstly, a brain wave sensor device 200 mounted to a user 11 detects an intention of the user to touch any of the icon 21 and the icon 22 which function as the pseudo input interface with a pointer 12. Then, when the intention of the user is detected, processing associated therewith is performed, according to the detected intention of the user. For example, when the intention of the user to touch (so-called short press) a start icon 21, is detected, the terminal device 100 performs the processing relating to the display of a start screen identified on the basis of information of the intention. At this time, the processing is performed on the basis of the detected intention of the user 11, and it is not necessary to actually touch the icon 21 with the pointer 12 of the user 11. In other words, regardless of whether the user operates the icons 21 and 22, processing corresponding to the detected intention is performed.

FIG. 8A is a table conceptually illustrating an operation identification table stored in a memory 212 of the brain wave sensor device 200 according to the second embodiment of the present disclosure. Specifically, the table stores feature points of brain wave signals of the user who performs operation inputs in a pseudo manner, sampled in advance, and the table is used to determine that the user intends to perform what kind of pseudo operation. According to FIG. 8A, an item of feature point information and an item of operation content information are stored in association with each item of operation input ID information. The brain wave of the user is sampled in advance when the user intends to perform an operation to each of the icons functioning as the pseudo input interface. The feature point information is information on a characteristic peak identified on the basis of a waveform obtained from the sampled brain wave. The operation content information is information indicating the content of a pseudo operation performed by the user when each item of the feature point information is obtained and is used to identify what operation is performed on which icon. In the present embodiment, for example, a feature point of a brain waveform detected by the brain wave sensor 211 is compared with each feature point stored in the operation identification table of FIG. 8A, and when the feature point of the detected brain waveform matches an item of feature point information "'S1", "touch icon 21 (short press)" is identified as pseudo operation content information. Then, from the brain wave sensor device 200, an item of operation input ID information "Q1" corresponding to "touch" input is output as the intention information to the terminal device 100.

Figures 8B, 9:
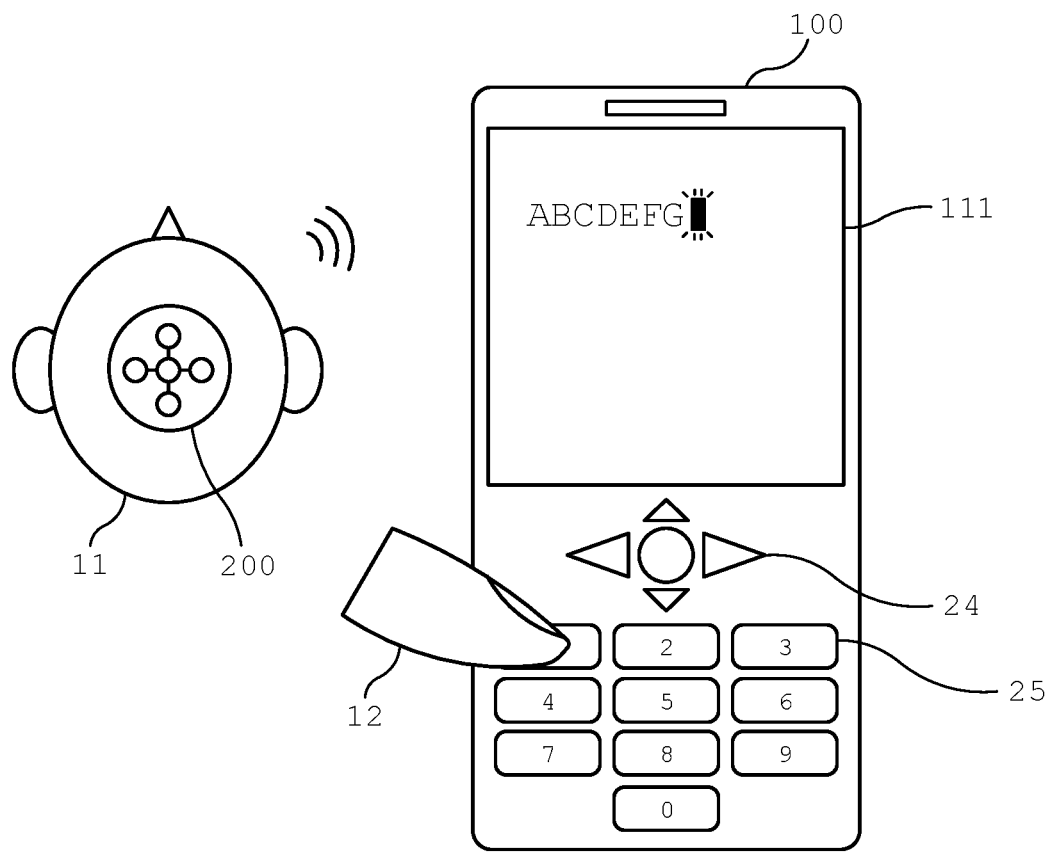
FIG. 8B is a table conceptually illustrating a processing identification table stored in a memory 113 of a terminal device 100 according to the second embodiment of the present disclosure.
FIG. 9 is a diagram conceptually illustrating processing in a system according to a third embodiment of the present disclosure.

FIG. 8B is a table conceptually illustrating a processing identification table stored in a memory 113 of the terminal device 100 according to the second embodiment of the present disclosure. Specifically, the table stores the operation input ID information received as the intention information from the brain wave sensor device 200, in association with the content of processing identified on the basis of the operation input ID information. According to FIG. 8B, an item of the operation input ID information and the content of processing are stored in association with each item of processing ID information. The operation input ID information is information in which a pseudo operation which the user intends to input is identified by the brain wave sensor device 200. The processing content information is information indicating the content of processing executed by the processor 112 on the basis of a predetermined pseudo operation having been performed on the pseudo input interface by the user. In the present embodiment, for example, when the item of the operation input ID information "Q1" is received from the brain wave sensor device 200, the processor 112 refers to the processing identification table, determines processing content information ("display the start screen") associated with the item of the operation input ID information "Q1", and executes processing (communication with the server device 300, drawing processing, etc.) to display the start screen.

In the present embodiment, a processing sequence performed between the terminal device 100, the brain wave sensor device 200, and the server device 300 and a process performed by the processor 112 of the terminal device 100 are not illustrated. However, as in the first embodiment, predetermined processing is performed by detecting the intention of the user to operate the icons 21 and 22 by the brain wave sensor device 200. Meanwhile, even if the user's actual operations on the icons 21 and 22 functioning as the pseudo input interface are performed, the terminal device 100 does not perform processing to detect the actual operation input nor use the actual operation inputs as a trigger for displaying the start screen.

As described above, in the present embodiment, the brain wave sensor device 200 detects an intention of the user to perform an operation, and thereby it is possible to cause the terminal device 100 to perform corresponding processing. Meanwhile, the terminal device 100 displays the icons 21 and 22 functioning as the pseudo input interface, and although the execution of the processing itself is performed on the basis of an intention of the user detected by the brain wave sensor device 200, it is possible to give an operational feeling to the user as if he/she actually operates the device 100.

THIRD EMBODIMENT

In the first embodiment, the entire display 111 and the hardware key 116 which function as the pseudo input interface in the title screen have been described. In the second embodiment, at least partial areas of the display, specifically, the icons 21 and 22 which function as the pseudo input interface in the title screen have been described. In the third embodiment, a description is given of hardware keys 24 and 25 fixedly provided on a housing of a terminal device 100 and caused to function as the pseudo input interface, instead of causing the display 111 or the icons 21 and 22 displayed on the display 111 to function as the pseudo input interface. Note that the present embodiment is similar to the first embodiment in configuration, processing, and procedure, except for the points described below specifically. Therefore, detailed description thereof will be omitted.

FIG. 9 is a diagram conceptually illustrating processing in a system according to a third embodiment of the present disclosure. According to FIG. 9, the terminal device 100 includes the hardware keys 24 including direction keys and an enter key, and the hardware keys 25 including numeric keys provided corresponding to the numerals 1 to 0, and the hardware keys 24 and 25 are fixedly provided on a surface of the housing. In the present embodiment, these hardware keys 24 and 25 function as a pseudo input interface. In the example of FIG. 9, a description will be given of inputting characters (numbers and the like) by the user in a screen of a character input application displayed on a display 111. Specifically, the display 111 shows a cursor (next to the right side of "G") indicating a position to which next character is to be input, together with characters ("A" to "G") having been input.

Firstly, a brain wave sensor device 200 mounted to a user 11 detects an intention of the user to press with a pointer 12 any of the hardware keys 24 and 25 functioning as the pseudo input interface. Then, when the intention of the user is detected, processing associated therewith is performed, according to the detected intention of the user. For example, when the intention of the user to press a left arrow key of the hardware keys 24 is detected, the terminal device 100 performs processing identified on the basis of information of the intention. At this time, the processing is performed on the basis of the detected intention of the user 11, and it is not necessary to actually press any of the hardware keys 24 with the pointer 12 of the user 11. In other words, regardless of whether the user operates any of the hardware keys 24 or 25, processing corresponding to the detected intention is performed.

FIG. 10A is a table conceptually illustrating an operation identification table stored in a memory 212 of the brain wave sensor device 200 according to the third embodiment of the present disclosure. Specifically, the table stores feature points of brain wave signals of the user who performs operation inputs in a pseudo manner, sampled in advance, and the table is used to determine that the user intends to perform what kind of pseudo operation. According to FIG. 10A, an item of feature point information and an item of operation content information are stored in association with each item of operation input ID information. A brain wave of the user is sampled in advance when the user intends to press any of the hardware keys 24 and 25 functioning as the pseudo input interface. The feature point information is information on a characteristic peak identified on the basis of a waveform obtained from the sampled brain wave. The operation content information is information indicating the content of a pseudo operation performed by the user when each item of the feature point information is obtained and is used to identify that the user intends to perform an operation on which hardware key. In the present embodiment, for example, a feature point of a brain waveform detected by the brain wave sensor 211 is compared with each feature point stored in the operation identification table of FIG. 10A, and when the feature point of the detected brain waveform matches an item of feature point information "U1", "operation of up arrow key" is identified as pseudo operation content information. Then, from the brain wave sensor device 200, an item of operation input ID information "R1" corresponding to "operation of up arrow key" is output as the intention information to the terminal device 100.

FIG. 10B is a table conceptually illustrating a processing identification table stored in a memory 113 of the terminal device 100 according to the third embodiment of the present disclosure. Specifically, the table stores the operation input ID information received as the intention information from the brain wave sensor device 200, in association with the content of processing identified on the basis of the operation input ID information. According to FIG. 10B, an item of the operation input ID information and the content of processing are stored in association with each item of the processing ID information. The operation input ID information is information in which a pseudo operation which the user intends to input is identified by the brain wave sensor device 200. The processing content information is information indicating the content of processing executed by the processor 112 on the basis of a predetermined pseudo operation having been performed on the pseudo input interface by the user. In the present embodiment, for example, when the item of the operation input ID information "R1" is received from the brain wave sensor device 200, the processor 112 refers to the processing identification table, determines processing content information ("upward movement of cursor") associated with the item of the operation input ID information "R1", and executes processing to move the cursor displayed on the display 111 upward.

In the present embodiment, a processing sequence performed between the terminal device 100, the brain wave sensor device 200, and the server device 300 and a process performed by the processor 112 of the terminal device 100 are not illustrated. However, as in the first and second embodiments, predetermined processing is performed by detecting an intention of the user to operate any of the hardware keys 24 and 25 by the brain wave sensor device 200. Meanwhile, even if a user's actual operation is performed on any of the hardware keys 24 and 25 functioning as the pseudo input interface, the terminal device 100 does not perform processing to detect the actual operation input nor use the actual operation input as a trigger for displaying a start screen.

As described above, in the present embodiment, the brain wave sensor device 200 detects an intention of the user to perform an operation, and thereby it is possible to cause the terminal device 100 to perform corresponding processing. Meanwhile, the terminal device 100 includes the hardware keys 24 and 25 functioning as the pseudo input interface, and the user can have an operational feeling as if he/she actually operates the terminal device 100 although the processing itself is performed on the basis of the intention detected by the brain wave sensor device 200. In particular, the hardware key enables the user to directly feel the click feeling of the key, and higher operational feeling can be obtained.

FOURTH EMBODIMENT

In the first to third embodiments, a description has been given of the brain wave sensor device 200 which detects a brain wave of a user, compares a brain wave of the user sampled in advance with the detected brain wave to identify information on an intention of the user will be described. In the fourth embodiment, signals obtained by performing processing, such as A/D conversion, on brain waves of a user detected by electrodes El to En are transmitted to a terminal device 100, and intention information on an intention of the user is identified in a processor 112 of the terminal device 100. Note that the present embodiment is similar to the first to third embodiments in configuration, processing, and procedure, except for the points described below specifically. Therefore, detailed description thereof will be omitted.

In the present embodiment, as described above, to identify the intention information on the intention of the user in the processor 112 of the terminal device 100, the operation identification tables illustrated in FIGS. 4A, 8A, and 10A are stored in the memory 113 of the terminal device 100. Then, between S12 and S13 shown in FIG. 5, the intention information (T11) is received in the first to third embodiments, but a brain wave signal detected by the brain wave sensor 211 is received in the present embodiment. Then, when receiving the brain wave signal, the processor 112 refers to the operation identification tables stored in the memory 113 to identify the intention information on the intention of the user. Then, on the basis of the identified intention information on the intention of the user, processing based on the intention information on the intention of the user is performed, as in the first to third embodiments. The subsequent processing is the same as those in the first to third embodiments.

As described above, in the present embodiment, the brain wave sensor device 200 detects an intention of the user to perform an operation, and thereby it is possible to cause the terminal device 100 to perform corresponding processing. Meanwhile, the terminal device 100 includes the hardware keys 24 and 25 functioning as the pseudo input interface, and the user can have an operational feeling as if he/she actually operates the terminal device 100 although the processing itself is performed on the basis of the intention detected by the brain wave sensor device 200.

Others

In the first to fourth embodiments, use of the brain wave sensor device 200 has been described. However, in the present disclosure, the intention information on the intention of the user may only be detected, and it is possible to use various signals in addition to the brain wave. As an example, it is also possible to use a sensor device configured to detect an electric signal detected upon movement of a muscle to which an intention of the user is transmitted from a brain.

In addition, it is also possible to configure the system by appropriately combining or replacing component elements described in the above embodiments.

The processing and procedures described herein may also be implemented not only by those explicitly stated for the embodiments but also by software, hardware, or any combination thereof. Specifically, the processing and procedures described herein are achieved by implementing logic corresponding to the processing, in a medium, such as an integrated circuit, volatile memory, non-volatile memory, magnetic disk, or optical storage. Furthermore, the processing and procedures described herein may be implemented as computer programs so that various computers including terminal devices and server devices are caused to execute the computer programs.

Even though the processing and procedures described herein are described as being performed by a single device, software, component, or module, such processing and procedures may be performed by a plurality of devices, a plurality of software applications, a plurality of components, and/or a plurality of modules. Furthermore, even though various information is described herein as being stored in a single memory or storage unit, such information may be distributed and stored in a plurality of memories included in a single device or in a plurality of memories distributed and arranged in a plurality of devices. Furthermore, the software and hardware elements described herein may be achieved by being integrated with each other into a small number of component elements or by being divided into a large number of component elements.

The terminal device, program, method, and system being thus described, it will be apparent that the same may be varied in many ways. Such variations are not to be regarded as a departure from the spirit and scope of the invention, and all such modifications as would be apparent to one of ordinary skill in the art are intended to be included within the scope of the following claims.

What is claimed is:

1. A terminal device comprising:
   a pseudo input interface configured to make a user to perceive a pseudo operation;
   an external communication interface configured to receive intention information indicating an intention of the user from a sensor device, the sensor device being wiredly or wirelessly connected to the external communication interface, the sensor device detecting the intention of the user who intends to perform an intended operation with respect to the pseudo input interface;
   a memory configured to store computer readable instructions; and
   a processor configured to execute the computer readable instructions so as to:
      identify the intended operation by the user based on the intention information received by the external communication interface, regardless of an actual operation perceived by the user with respect to the pseudo input interface; and
      perform a processing corresponding to the identified intended operation.

2. The terminal device according to claim 1, further comprising:
   a display configured to show an image,
   wherein the pseudo operation perceived by the user is an operation with respect to the display.

3. The terminal device according to claim 1, further comprising:
   a display configured to show an image,
   wherein the pseudo input interface is an icon displayed on the display as the image so that when the icon is observed by the user, the pseudo operation is perceived by the user.

4. The terminal device according to claim 1,
   wherein the pseudo input interface is an operation key fixedly provided on a housing of the terminal device.

5. The terminal device according to claim 1,
   wherein the external communication interface transmits and receives predetermined information to and from a server device that is remotely installed, and
   the processing corresponds to the transmission and the reception of the predetermined information to and from the server device.

6. The terminal device according to claim 1,
   wherein the processor executes the processing corresponding to the identified intended operation without activating the actual operation performed with respect to the pseudo input interface by the user, even when the pseudo input interface is actually operated by the user.

7. The terminal device according to claim 1,
   wherein the sensor device includes one or a plurality of electrodes for detecting a brain wave of the user.

8. The terminal device according to claim 1,
   wherein the processor is configured to provide feedback corresponding to the identified intended operation to the user.

9. A system comprising:
   the terminal device according to claim 1; and
   a sensor device wiredly or wirelessly connected to the terminal device to detect the intention of the user perceiving one or a plurality of operation inputs with respect to the pseudo input interface of the terminal device.

10. A non-transitory computer-readable storage medium storing a computer program product embodying computer readable instructions for causing a computer to execute a process by a processor so as to perform the steps of:
    making a user to perceive a pseudo operation via a pseudo input interface;
    receiving intention information indicating an intention of the user from a sensor device, the sensor device detecting the intention of the user who intends to perform an intended operation with respect to the pseudo input interface;
    identifying the intended operation by the user based on the intention information, regardless of an actual operation perceiving by the user with respect to the pseudo input interface; and
    performing a processing corresponding to the identified intended operation.

11. A method for causing a processor in a computer to execute a process, the method comprising executing on the processor the steps of:
    making a user to perceive a pseudo operation via a pseudo input interface;
    receiving intention information indicating an intention of the user from a sensor device, the sensor device detecting the intention of the user who intends to perform an intended operation with respect to the pseudo input interface;
    identifying the intended operation by the user based on the intention information regardless of an actual operation perceiving by the user with respect to the pseudo input interface; and
    performing a processing corresponding to the identified intended operation.

12. A terminal device comprising:
    a pseudo input interface configured to make a user to perceive a pseudo operation;
    an external communication interface configured to wiredly or wirelessly receive a signal indicating an intention of the user who intends to perform an intended operation with respect to the pseudo input interface;
    a memory configured to store computer readable instructions and a correspondence relationship between the signal and the intention of the user; and
    a processor configured to execute the computer readable instructions so as to:
       generate intention information indicating the intention of the user based on the received signal and the correspondence relationship stored in the memory, regardless of an actual operation perceived by the user with respect to the pseudo input interface;
       identify the intended operation by the user in response to the generated intention information; and
       execute a processing corresponding to the identified intended operation.

* * * * *